(12) United States Patent
Luttrull et al.

(10) Patent No.: US 10,076,671 B2
(45) Date of Patent: Sep. 18, 2018

(54) APPARATUS FOR RETINA PHOTOTHERAPY

(71) Applicant: Ojai Retinal Technology, LLC, Ojai, CA (US)

(72) Inventors: Jeffrey K. Luttrull, Ojai, CA (US); Benjamin W. L. Margolis, Oakland, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 5 days.

(21) Appl. No.: 15/201,107

(22) Filed: Jul. 1, 2016

(65) Prior Publication Data

US 2016/0339264 A1 Nov. 24, 2016

Related U.S. Application Data

(63) Continuation-in-part of application No. 14/332,674, filed on Jul. 16, 2014, which is a continuation-in-part
(Continued)

(51) Int. Cl.
*A61N 5/06* (2006.01)
*A61F 9/008* (2006.01)
*A61N 5/067* (2006.01)

(52) U.S. Cl.
CPC ........ *A61N 5/0622* (2013.01); *A61F 9/00821* (2013.01); *A61F 9/00817* (2013.01);
(Continued)

(58) Field of Classification Search
CPC ............ A61N 5/0622; A61N 2005/067; A61N 2005/0626; A61N 2005/0642;
(Continued)

(56) References Cited

U.S. PATENT DOCUMENTS 3,408,593 A 10/1968 Hurwitz, Jr.
4,048,011 A 9/1977 Kovin et al.
(Continued)

FOREIGN PATENT DOCUMENTS

WO WO 2006005038 A2 1/2006
WO WO 2007035855 A2 3/2007
(Continued)

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.
(Continued)

*Primary Examiner* — Catherine Voorhees
(74) *Attorney, Agent, or Firm* — Kelly & Kelley, LLP

(57) ABSTRACT

A process for using a retinal photostimulation device involves limiting multiple or repeated uses of the device during a particular treatment cycle. Ordinarily a physician would not want to repeat multiple photostimulation treatments on a patient in a short period time. The process would prevent such retreatment during a single treatment cycle where the retina for any subsequent treatment biometrically matches the retina for an earlier treatment. Such subsequent treatments would be permitted within a predefined period of time after the earlier treatment. Such subsequent treatment may also be permitted where the retinas do not biometrically match.

9 Claims, 8 Drawing Sheets

Related U.S. Application Data of application No. 13/798,523, filed on Mar. 13, 2013, which is a continuation-in-part of application No. 13/481,124, filed on May 25, 2012, now Pat. No. 9,381,115.

(52) U.S. Cl.
CPC ............ *A61F 2009/00863* (2013.01); *A61N 2005/067* (2013.01); *A61N 2005/0626* (2013.01); *A61N 2005/0642* (2013.01)

(58) Field of Classification Search
CPC ............ A61F 9/00821; A61F 9/00817; A61F 2009/00863
USPC .............................................. 607/89; 606/4–6
See application file for complete search history.

(56) References Cited

U.S. PATENT DOCUMENTS

| | | | |
|---|---|---|---|
| 4,176,325 A | 11/1979 | Kajimura et al. | |
| 4,194,114 A | 3/1980 | Pankratov et al. | |
| 4,410,365 A | 10/1983 | Glukhovsky et al. | |
| 4,695,733 A | 9/1987 | Pesavento | |
| 4,730,335 A | 3/1988 | Clark et al. | |
| 4,791,634 A | 12/1988 | Miyake | |
| 4,865,029 A | 9/1989 | Pankratov et al. | |
| 4,879,722 A | 11/1989 | Dixon et al. | |
| 4,930,504 A | 6/1990 | Diamantopoulos et al. | |
| 4,933,944 A | 6/1990 | McGraw | |
| 4,935,931 A | 6/1990 | McGraw | |
| 4,961,079 A | 10/1990 | Owens et al. | |
| 4,967,416 A | 10/1990 | Esterowitz et al. | |
| 5,037,421 A | 8/1991 | Boutacoff et al. | |
| 5,067,951 A | 11/1991 | Greve | |
| 5,085,492 A | 2/1992 | Kelsoe et al. | |
| 5,088,803 A | 2/1992 | Buzawa | |
| 5,147,354 A | 9/1992 | Boutacoff et al. | |
| 5,372,595 A | 12/1994 | Gaasterland et al. | |
| 5,394,199 A | 2/1995 | Flower | |
| 5,430,756 A | 7/1995 | Hanihara | |
| 5,520,680 A | 5/1996 | Shapshay et al. | |
| 5,651,019 A | 7/1997 | Goldberg et al. | |
| 5,982,789 A | 11/1999 | Marshall et al. | |
| 6,066,128 A | 5/2000 | Bahmanyar et al. | |
| 6,106,513 A * | 8/2000 | McMillen | A61F 9/008 606/10 |
| 6,208,769 B1 | 3/2001 | Pankratov | |
| 6,222,869 B1 | 4/2001 | Marshall et al. | |
| 6,327,291 B1 | 12/2001 | Marshall | |
| 6,377,599 B1 | 4/2002 | Marshall | |
| 6,540,391 B2 | 4/2003 | Lanzetta et al. | |
| 6,681,185 B1 | 1/2004 | Young et al. | |
| 6,715,877 B2 | 4/2004 | Molebny | |
| 6,733,490 B1 | 5/2004 | Falsini et al. | |
| 6,813,942 B1 | 11/2004 | Vozhdaev et al. | |
| 6,889,695 B2 | 5/2005 | Pankratov et al. | |
| 7,227,196 B2 | 6/2007 | Burgener, II et al. | |
| 7,387,785 B1 | 6/2008 | Rudin et al. | |
| 7,452,081 B2 | 11/2008 | Wiltberger et al. | |
| 7,645,276 B2 | 1/2010 | Pankratov et al. | |
| 7,763,828 B2 | 7/2010 | Talwar et al. | |
| 7,766,903 B2 | 8/2010 | Blumenkranz et al. | |
| 7,766,904 B2 | 8/2010 | McGowan, Sr. et al. | |
| 7,771,417 B2 | 8/2010 | Telfair et al. | |
| 7,909,816 B2 | 3/2011 | Buzawa | |
| 8,454,161 B2 | 6/2013 | Su et al. | |
| 2002/0099363 A1 | 7/2002 | Woodward et al. | |
| 2002/0120255 A1 | 8/2002 | Sotiropoulos et al. | |
| 2002/0165525 A1 | 11/2002 | Nakamura | |
| 2007/0055222 A1 * | 3/2007 | Hohla | A61B 5/117 606/12 |
| 2008/0015553 A1 | 1/2008 | Zacharias | |
| 2009/0054879 A1 * | 2/2009 | Berry | A61F 9/008 606/5 |
| 2010/0152716 A1 | 6/2010 | Previn et al. | |
| 2010/0168724 A1 | 7/2010 | Sramek et al. | |
| 2010/0204571 A1 * | 8/2010 | DellaVecchia | A61B 3/12 600/427 |
| 2010/0249760 A1 | 9/2010 | Blumenkranz et al. | |
| 2010/0290007 A1 | 11/2010 | Van de Velde | |
| 2011/0196350 A1 | 8/2011 | Friedman et al. | |
| 2011/0205019 A1 * | 8/2011 | Wellhoefer | G06F 19/3406 340/5.82 |
| 2012/0095349 A1 * | 4/2012 | Peyman | A61B 3/10 600/473 |
| 2013/0116670 A1 * | 5/2013 | Artsyukhovich | A61B 3/1233 606/4 |
| 2013/0116672 A1 | 5/2013 | Yee | |

FOREIGN PATENT DOCUMENTS

| | | | | |
|---|---|---|---|---|
| WO | WO 2007051118 A2 * | 5/2007 | ............ | A61B 5/117 |
| WO | WO 2007106521 A2 | 9/2007 | | |

OTHER PUBLICATIONS

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Small Beam Diameter Scanning Galvo Mirror Systems; Thorlabs; 1999-2013, 4 pgs.

* cited by examiner

APPARATUS FOR RETINA PHOTOTHERAPY

RELATED APPLICATION

This application is a continuation-in-part of U.S. application Ser. No. 14/332,674, which is a continuation-in-part of U.S. application Ser. No. 13/798,523, filed on Mar. 13, 2013, which is a continuation-in-part of U.S. application Ser. No. 13/481,124, filed May 25, 2012 (now U.S. Pat. No. 9,381,115).

BACKGROUND OF THE INVENTION

The present invention is generally directed to a system for reliably and comfortably providing retina treatment to patients. More particularly, this invention is directed to a system able to accommodate patients of various shapes and sizes in a comfortable manner and more effectively target and treat patient's retinas.

Prior art systems and devices were not comfortable for patients to use and were inefficient at targeting and treating patient's retinas. Such prior art systems presented cramped or close quarters for patients to squeeze or jam themselves into. Such could cause pain or discomfort for the patient. In certain instances, it may also result in injury if the patient cannot maintain the position or falls out of position either to the floor or into a piece of furniture or equipment.

In such uncomfortable positions, it was difficult for a patient to remain sufficiently immobile long enough for a treatment cycle to complete. Treatment would be prolonged or restarted for multiple cycles if the patient moved during the treatment.

Thus, there is a need for a system and/or device that provide a more comfortable treatment position for a patient and more reliably and efficiently provides treatment to a patient's retina. The present invention fulfills these needs and provides other related advantages.

SUMMARY OF THE INVENTION

The present invention is directed to a process for performing retinal photostimulation, including providing a retinal photostimulation device comprising a radiant energy source and projection optics configurable so as to target a retina of a person, a camera configurable so as to focus on and capture an image of the retina of the person simultaneously with the targeting of the retina by the radiant energy source and projection optics, a monitor configurable so as to display the image of the retina captured by the camera, and electronic memory configured to record one or more images of the retina captured by the camera. A user then begins a treatment cycle for a patient using the retinal photostimulation device. The treatment cycle includes registering the patient for a first treatment during the treatment cycle.

Registering includes recording in a patient file in the electronic memory the patient's name, a date and time for the first treatment, and an image of a retina of the patient corresponding to the first treatment. A plurality of radiant beams from the radiant energy source is then applied to at least a portion of the retina of the patient so as to effect the first treatment contemporaneously with the date and time for the first treatment. A post-treatment image of the retina of the patient corresponding to the first treatment is then recorded in the patient file. The treatment cycle for the patient is then ended.

The process may further include registering the patient for a second treatment during the treatment cycle. This registering for a second treatment includes recording in the patient database the patient's name, a date and time for the second treatment, and an image of a retina of the patient corresponding to the second treatment. The process may also include preventing application of the second treatment during the treatment cycle when the image of the retina of the patient corresponding to the second treatment biometrically matches the image of the retina of the patient corresponding to the first treatment. Application of the second treatment may also be prevented if the date and time for the second treatment is not within a predetermined retreatment window after the first treatment. Such a retreatment window may be a period of sixty minutes after the date and time for the first treatment.

Application of the second treatment during the treatment cycle may be permitted when the image of the retina of the patient corresponding to the second treatment does not biometrically match the image of the retina of the patient corresponding to the first treatment. In this instance, a post-treatment image of the retina of the patient corresponding to the second treatment may be recorded in the patient file.

The second treatment during the treatment cycle may also be permitted when the image of the retina of the patient corresponding to the second treatment biometrically matches the image of the retina of the patient corresponding to the first treatment and when the date and time for the second treatment is within a retreatment window after the first treatment. In this instance, the retreatment window is a period of sixty minutes after the date and time for the first treatment. The process may also permit multiple additional treatments of the same retina of patient within the retreatment window.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
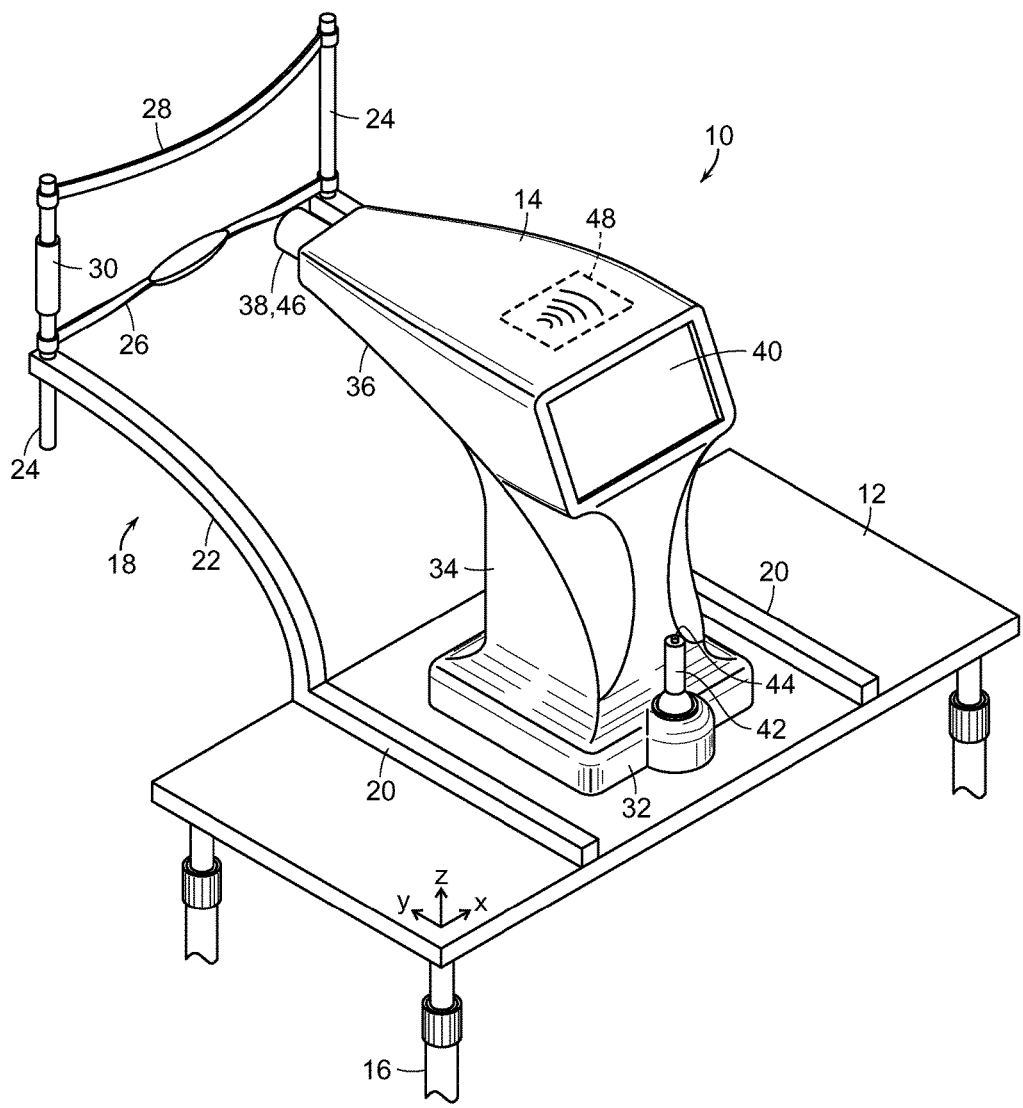
FIG. 1 is a perspective view of the retina phototherapy system of the present invention.
Figure 2:
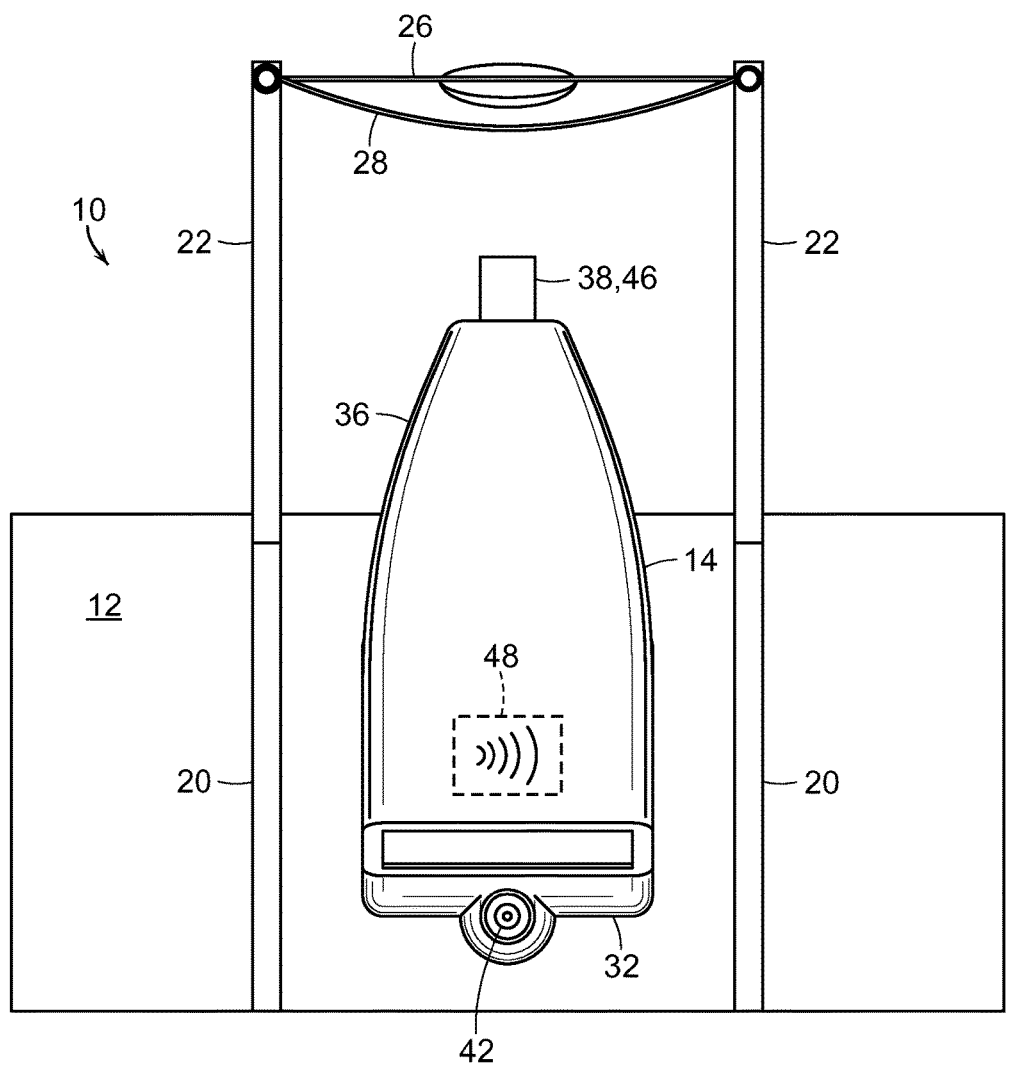
FIG. 2 is a top view of the retina phototherapy system of the present invention.
Figure 3:
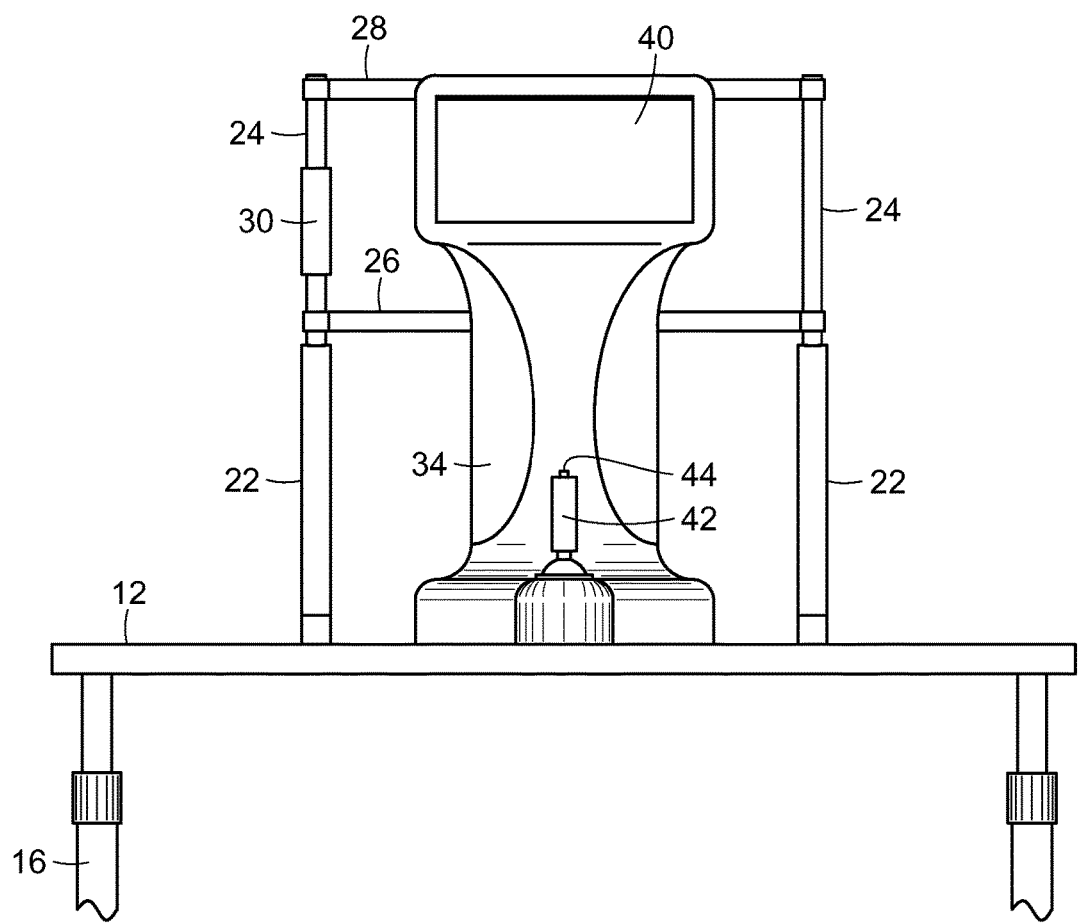
FIG. 3 is a back view of the retina phototherapy system of the present invention.
Figure 4:
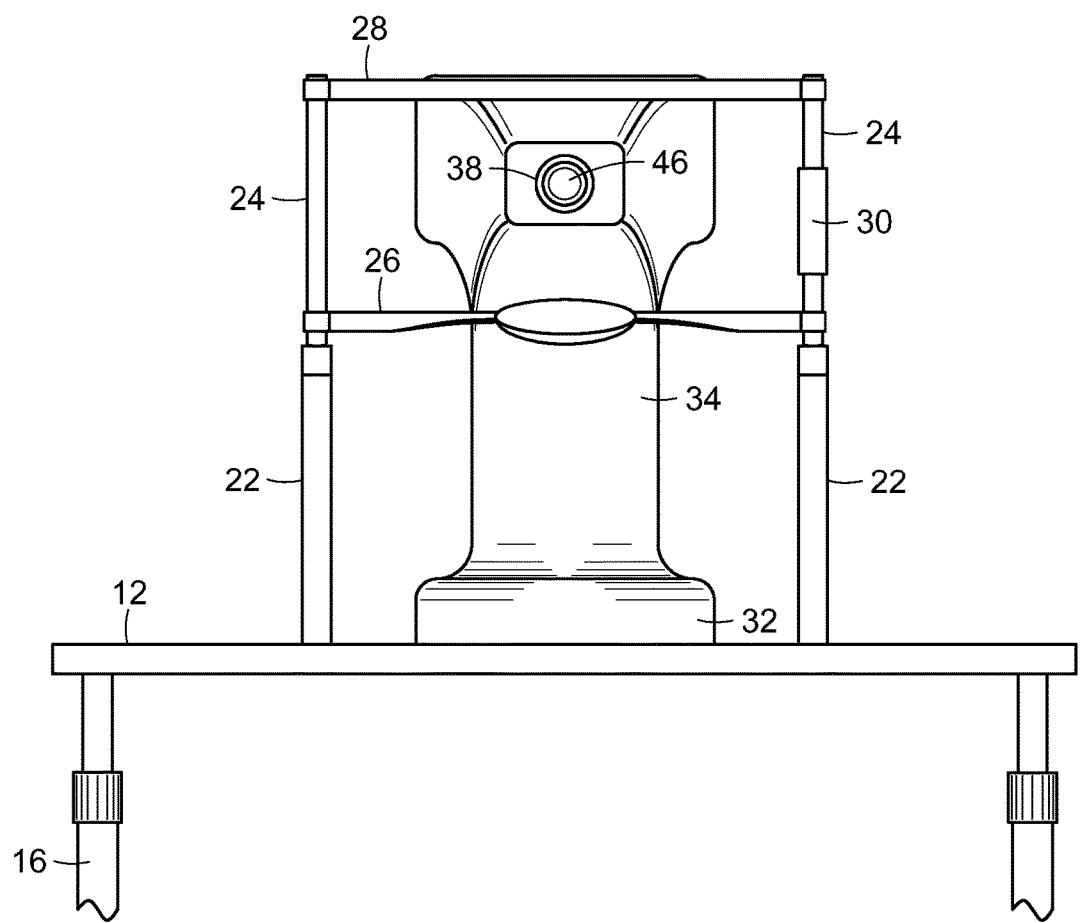
FIG. 4 is a front view of the retina phototherapy system of the present invention.
Figure 5:
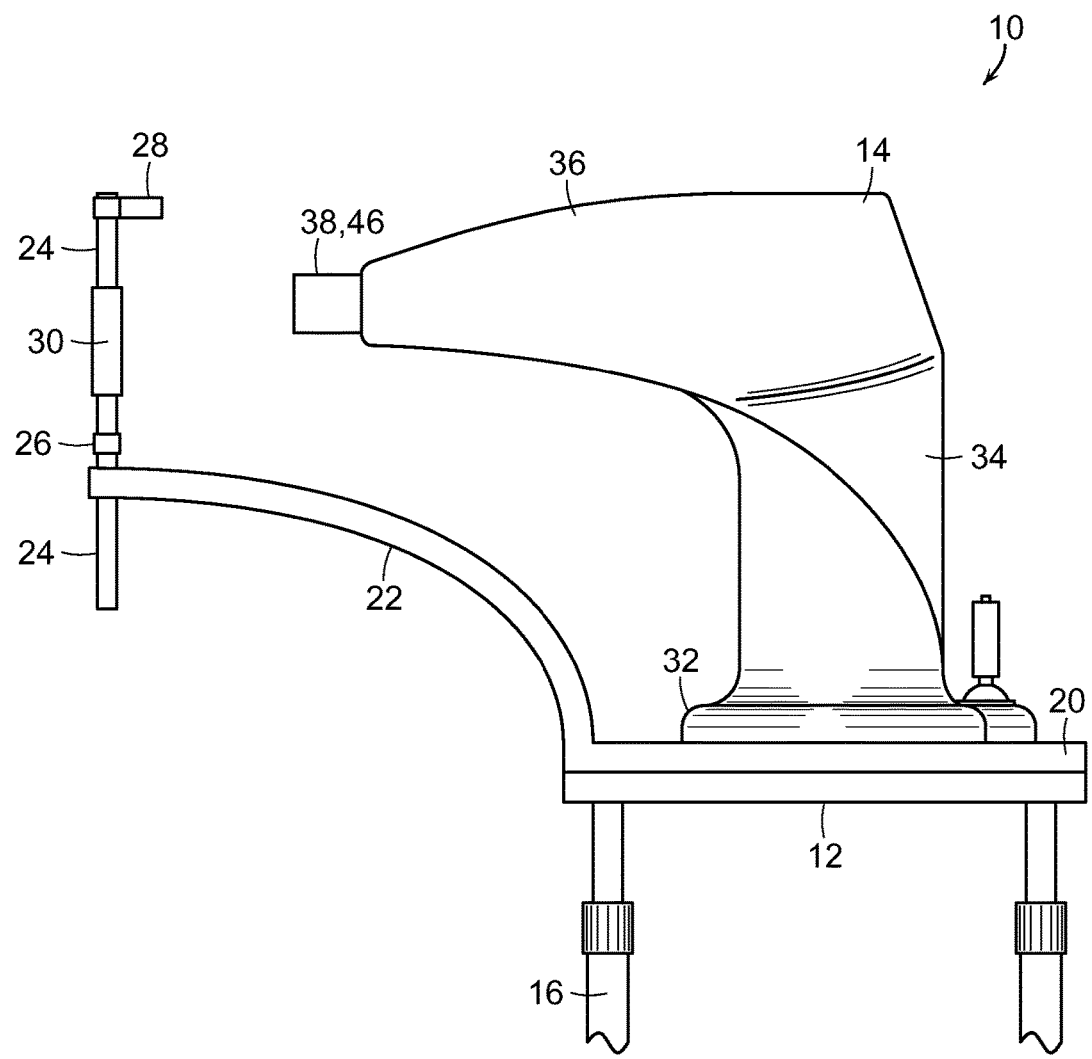
FIG. 5 is a side view of the retina phototherapy system of the present invention.

The present invention is generally directed to a system for treating a patient's retina with a radiant energy source, including but not limited to a laser. Throughout this description the use of "laser" on its own or as part of a larger assembly shall include any radiant energy source. The system, generally referred to by reference numeral 10 in FIGS. 1-7, consists primarily of a working surface 12 and a retina phototherapy device 14. The following description will refer to the relative position of various components in a 3-dimensional coordinate system, i.e., X, Y, and Z axes. Under this convention, the X-axis refers to lateral or side-to-side movement relative to the horizontal. The Y-axis refers to longitudinal or front-to-back movement relative to the horizontal. The Z-axis refers to vertical or up-and-down movement relative to the horizontal.

As illustrated in FIGS. 1-5, the working surface 12 is a generally horizontal, planar surface that rests on legs 16 or similar supports. The height of the legs 16 is preferably adjustable such that the position of the working surface 12 in the Z-axis is adjustable on a macro scale, i.e., units of feet or inches. The legs 16 may rest on the floor using pads or wheels (not shown), such that the legs are either stationary or moveable relative to the floor.

A headrest assembly 18 extends from the top of the working surface 12. A pair of base arms 20 are affixed to the top of the working surface in a generally parallel configuration in the longitudinal direction, i.e., along the Y-axis. Curved extension arms 22 are attached to the base arms 20 proximate to a leading edge 12a of the working surface 12. The curved extension arms 22 rise upward above the working surface 12 and extend forward of the leading edge 12a. A pair of uprights 24 extends vertically through a distal end of the extension arms 22, wherein the height of the uprights 24 relative to the working surface 12 is adjustable.

A chin rest 26 extends between a lower end of the uprights 22 and a forehead rest 28 extends between upper ends of the uprights 22. The chin rest 26 and forehead rest 28 are respectively configured to receive the chin and forehead of a person's face. An adjustment coupling 30 on the uprights 22 allows for the spacing of the chin rest 26 and forehead rest 28 to be adjustable relative to each other so as to accommodate faces of different sizes. As described above, the curved extension arms 22 rise above (in the direction of the Z-axis) and forward of (in the direction of the Y-axis) the working surface 12 so as to position the face of a person in front of the retina phototherapy device 14 as further described below.

The retina phototherapy device 14 generally resembles a self-standing, gun-like device having a flat base pad 32, a vertical stand 34, and a projecting barrel 36. A radiant energy source and projection optics 38, i.e., laser optics, extend from a distal end of the barrel 36. The laser optics 38 are preferably wide angle optics having a range of 110 degrees or greater (See FIG. 8). A display monitor or viewing screen 40 is disposed on a proximate end of the device 14, preferably proximate to the junction of the vertical stand 34 and the barrel 36. The base pad 32 rests on the top of the working surface 12 and is sufficiently large to provide a stable base for the device 14. The device 14 preferably has a unitized construction design as illustrated, wherein all components are contained within a housing. The housing of the device 14 preferably has a high-gloss, opalescent finish, and seams/modular junctions of a high tolerance, i.e., close fitting or low profile, for an aesthetically pleasing appearance. The high tolerance seams/modular junctions also prevent dust entry and dirt accumulation. The system 10 preferably has a modular construction such that its various components—working surface 12, device 14, and headrest assembly 18—may be easily removed and replaced in a short amount of time without substantial downtime. A defective or broken component may be easily removed and replaced with another component this is shipped overnight, for example.

A joystick 42 having a spherical contact junction provides multiple degrees of movement to control operation of the device 14. Multiple degrees of movement refers to movement in directions such as, front-to-back, side-to-side, up and down (z-axis adjustment), and clockwise/counterclockwise rotation. Certain of these degrees of movement of the joystick 42 are configurable to control movement of the device 14 across the working surface, particularly micromovements, in the X, Y, and Z axes, as well as, rotation in the horizontal X-Y plane. Others degrees of movement of the joystick 42 may also control focus of the laser optics 38 or a camera as described below. The joystick 42 may also have a button or switch 44 to begin treatment delivery for the laser optics 38 or device 14 overall.

The display/monitor 40 is connected to a camera 46, preferably IR but also capable of capturing visible light spectrums. The camera 46 is preferably disposed adjacent to or coaxially with the laser optics 38 such that both components focus on the same target. The joystick 42 may be configured to control the focus of the camera 46 or alter the type of lens being used or light wavelengths to be detected. The image projected on the display/monitor 40 by the camera 46 permits a user to observe exactly where the laser optics 38 are pointed, particularly when treating a patient's retina. The display/screen 40 preferably presents a hi-resolution image of the patient's retina from the camera 46. The camera 46 preferably includes a fixed or parfocal lens such that it can be used as a range finder and generally stays in focus when the magnification/focal length is changed. The camera 46 may be associated with a light source (not shown), as a ring or adjacent light. The light source is preferably an infrared (IR) light source to provide illumination for the camera 46 and avoid pupil constriction.

An LCD aperture (not shown) to shape or partially occlude the opening for the laser optics 38 is preferably associated with the laser optics 38. The monitor 40 preferably has touch screen functionality to allow for finger tracing selection of treatment subfields via the LCD aperture. Treatment subfields may be determined based upon automatic identification of different retina structures, i.e., optic nerve, to as to exclude these areas from treatment. The excluded areas may be used as a tracking or stabilization target.

The laser optics 38 and camera 46 preferably include auto focus and range finder features. The laser optics 38 and camera 46 preferably also include image and laser projection stabilization, tracking, and registration features. Optical correction circuitry may be included to achieve laser optics 38 and camera 46 image par focus. The device 14 also includes an electronic memory to record fundus images and transfer procedure information, i.e., completion of prescribed treatment, into patient records. Such information would preferably include name, treatment date, treatment areas, date of birth, patient identification number, etc.

The device 14 may also include a secure communication protocol, i.e., Wi-Fi, Bluetooth, cellular, or satellite, or similar connection 48 to wirelessly transmit the procedure information. The same information may be wirelessly transmitted to a billing department to execute billing upon completion of treatment. The same wireless connection 48 or a comparable wired connection port, i.e., USB or similar, can allow for the uploading or reconfiguring of laser parameters and accompanying software. The operator or doctor may also use this wireless connection 48 to input patient information via a laptop or electronic medical record system prior to treatment. These same communication protocol functions may also be performed using a wired connection, i.e., USB or Ethernet.

For movement of the device 14 across the working surface, there are generally two types of movement—macro-movement and micro-movement—both in the plane of the working surface 12 and vertically above the working surface 12. Macro-movement refers to movement of the device 14 across the working surface on an easily observable scale, i.e., in terms of inches, centimeters, or other similar distance, between the two base arms 20. Micro-movement refers to fine-tune positioning of the device 14 in relation to a person's retina. Such fine-tune positioning or micro-movement is accomplished through use of the joystick 44 as described above. The joystick controls position motors or other mechanisms (not shown) on the underside of the base 32.

Figure 6:
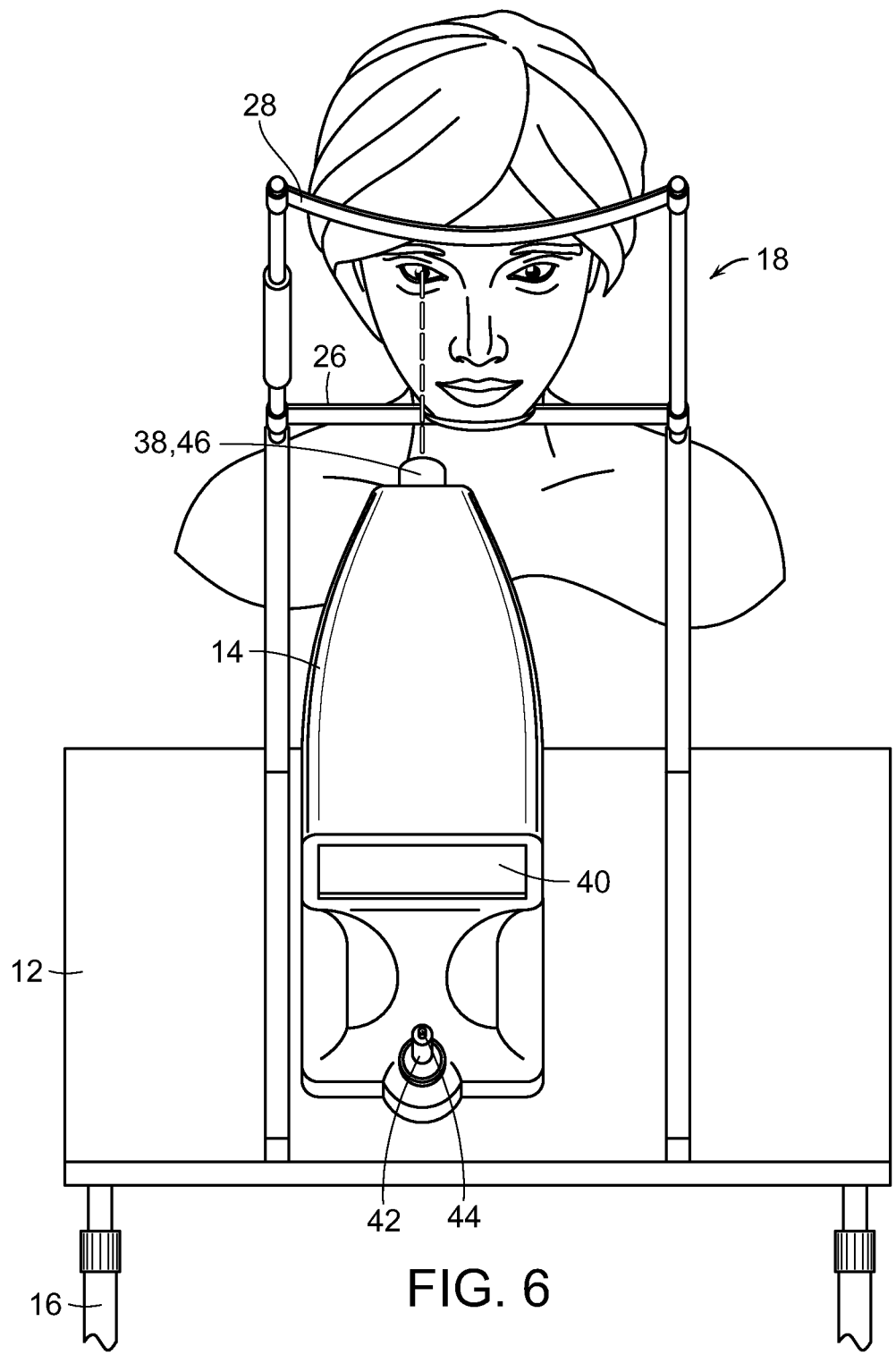
FIG. 6 is an elevated rear view of the retina phototherapy system being used on a right eye of a patient.
Figure 7:
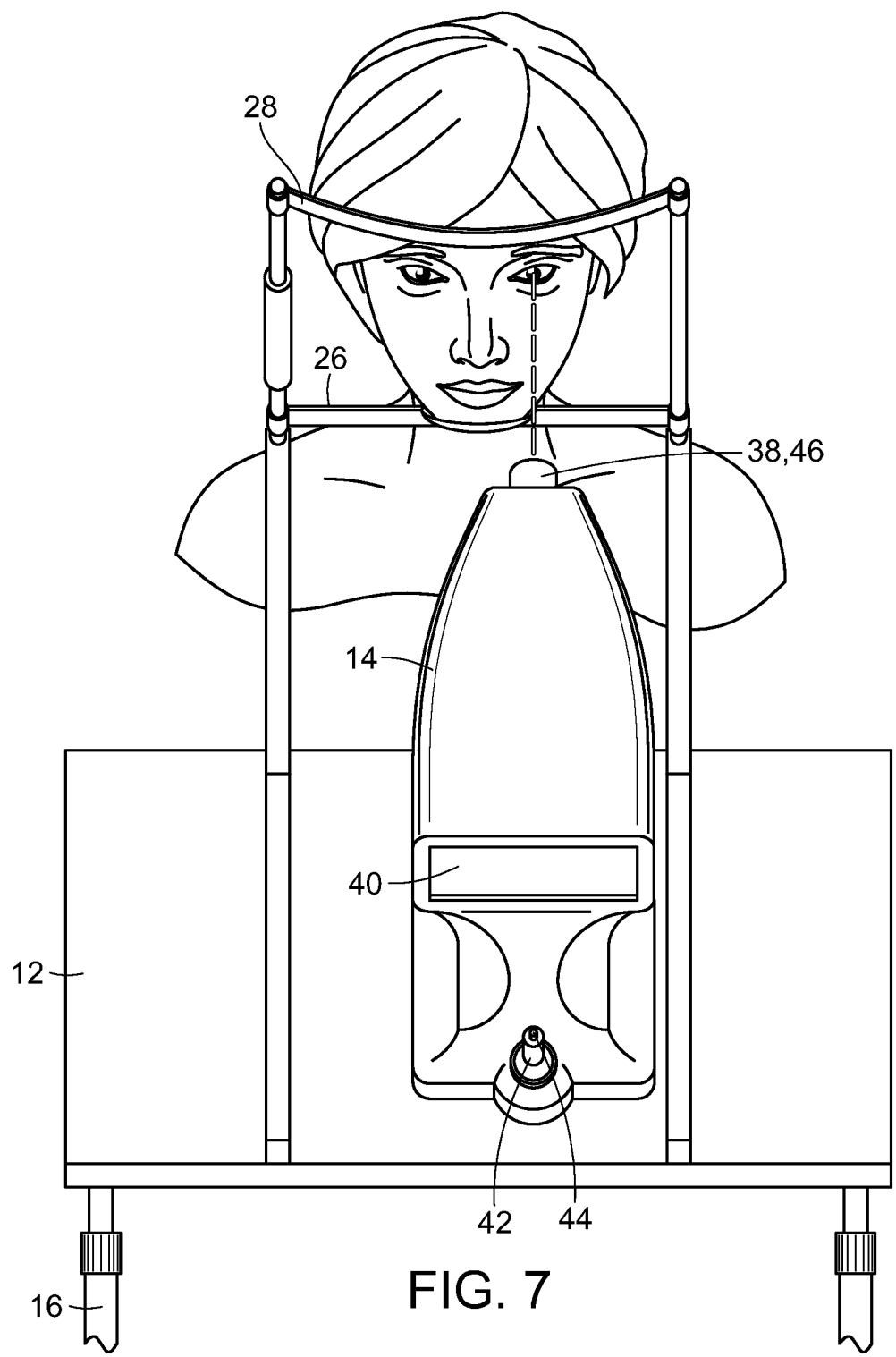
FIG. 7 is an elevated rear view of the retina phototherapy system being used on a left eye of a patient.

FIGS. 6 and 7 illustrate a person positioned in the headrest assembly 18, with their chin in the chin rest 26 and forehead in the forehead rest 28. The ergonomic configuration of the extension arms 22 in the headrest assembly 18 and the barrel 36 of the device 14 are designed to accommodate any type of head, body, or face by effectively reaching out to the patient rather than having the patient "jam" into the device. Patients with deep-set eyes, prominent brows, large chests, overweight, very tall, or very short can all be accommodated with this configuration.

The device 14 is preferably manually moved across the working surface 12—macro-movement—to generally align the laser optics 38 and camera 46 with the eye. The contact surfaces of the working surface 12 and the underside of the base 32 are preferably very low friction surfaces to facilitate the manual movement. A high friction plate (not shown) may be triggered to prevent further macro-movement once the device 14 is positioned. A visible patient fixation target or general positioning light (not shown) configured to illuminate the target area may be included to assist with this general alignment. The positioning light is projected into the eye coaxially with the laser optics 38 and camera 46. One may then use the joystick 42 and position motors to fine-tune the position and precise alignment of the device laser optics 38 and camera 46 with the eye.

In use, the operator brings the patient eye into view on the monitor 40 through the camera 46 and fine focuses using the degrees of movement of the joystick 42. The camera 46 projects an image of the retina in the back of the eye on the monitor 40. The monitor 40 or image projected by the camera 46 may include guide markings or a grid (not shown) to help accurately position the laser optics 38 in line with the eye and retina.

Once the retina is in fine focus and the treatment area is marked, the operator begins the treatment. Treatment is automatic until completed, even if occasionally interrupted by patient movement. The device 14 may capture multiple static images and/or videos of the patient's retina before, during and after treatment. The completion and thoroughness of treatment are preferably documented by retinal reflectance detected and recorded by the retinal fundus monitoring camera 46.

Figure 8:
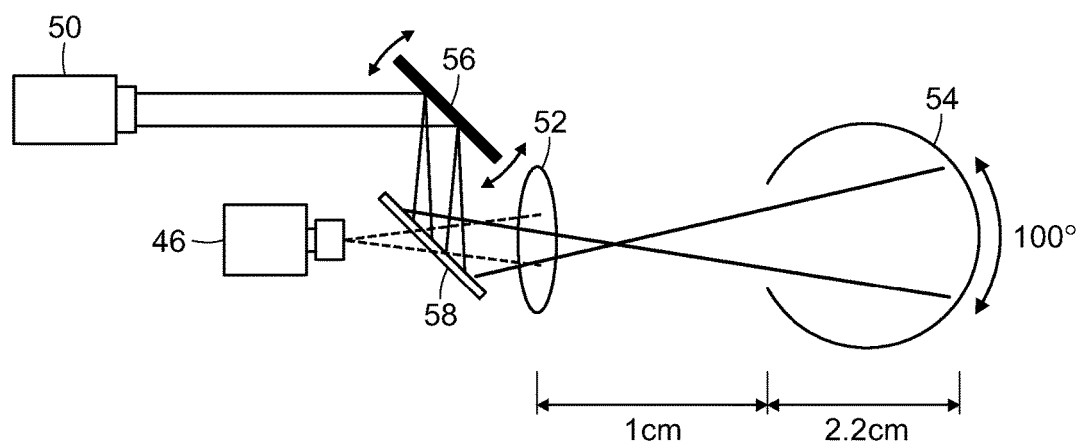
FIG. 8 is a block diagram of the configuration of the camera and laser optics.

FIG. 8 schematically illustrates a preferred configuration of the camera 46 and laser optics 38 in more detail. In this configuration, the camera 46 is aligned directly with the patient's retina 54 as shown. The radiant energy source 50 is shown offset from the camera 46 with its beam redirected by a steering mirror 56. The steering mirror reflects the radiant energy beam to a beam splitter 58. The beam splitter 58 is preferably of a reversed configuration so as to combine the reflected beams from the steering mirror 56. The beam splitter redirects the combined radiant energy beam through a lens 52 which focuses the same on the retina 54 in the back of the patient's eyeball. As illustrated, the radiant energy beam preferably has a target area range of about one hundred degrees around the curvature of the retina. The preferred distance between the laser optics 38 and the patient's eye is at least one centimeter. In order to project a beam in a spot that is large enough on the retina through the pupil, the beam must be focused through a point between the final optics or lens 52 and the pupil. This assumes a minimum pupil diameter of about five millimeters in the desired treatment lighting. These distances are just preferred ranges and other distances may work as intended with different configurations of energy sources 50, lenses 52, steering mirrors 56, and beam splitters 58. The camera 46 preferably operates through or around the lens 52 and beam splitter 58 without interfering with the path of the radiant energy beam.

In order to control the number of uses of the retinal photostimulation device on a patient, a user may define a treatment cycle for a particular patient. A treatment cycle would ordinarily be limited to a single application of the radiant energy source to the patient's retina. This is primarily to prevent overtreatment of the retina by multiple applications within a short period of time. Such may avoid a situation where multiple providers in the same office may accidentally repeat treatment on a patient using the same device. It is also useful in regulating the number of billable treatments utilizing the retinal photostimulation device to maintain the system and preserve operating life thereof.

During a particular treatment cycle, a user would register the patient for a first treatment during the treatment cycle. Upon first registering a patient, a user would create a patient file in the electronic memory of the system. Registering includes recording the patient's name, the date and time of the first treatment, and an image of a retina of the patient corresponding to the first treatment.

The first treatment is then applied to the retina. A plurality of radiant beams from the radiant energy source is directed through the optics to at least a portion of the retina of the patient. This first treatment is done contemporaneously with the recorded date and time of the first treatment. Then a post-treatment image of the retina of the patient corresponding to the first treatment is recorded in the patient file. Ordinarily, this would end the treatment cycle for the patient.

A physician may want to register the patient for a second treatment. Similar to registering the patient for the first treatment, registering for the second treatment includes recording the patient's name, the date and time for the second treatment, and an image of a retina of the patient corresponding to the second treatment. If this second treatment is during the same treatment cycle, the process may include preventing application of the second treatment during the treatment cycle when the image of the retina of the patient corresponding to the second treatment biometrically matches the image of the retina of the patient corresponding to the first treatment.

Application of the second treatment may also be prevented if the date and time for the second treatment is not within a predetermined retreatment window after the first treatment. Such a retreatment window may be a period of sixty minutes after the date and time for the first treatment. While a physician may want to prevent multiple treatments of the device, the retreatment window is intended to allow a physician to repeat a treatment if the first treatment was unsuccessful or if, in the physician's judgment, the patient's retina requires additional treatment.

Application of the second treatment during the treatment cycle may be permitted when the image of the retina of the patient corresponding to the second treatment does not biometrically match the image of the retina of the patient corresponding to the first treatment. Such may occur where the physician is treating both eyes of the patient. Where the second treatment is permitted, a post-treatment image of the retina of the patient corresponding to the second treatment may be recorded in the patient file.

In the case of the retreatment window discussed above, a second treatment during the treatment cycle may be permitted when the image of the retina of the patient corresponding to the second treatment biometrically matches the image of the retina of the patient corresponding to the first treatment and when the date and time for the second treatment is within the retreatment window after the first treatment. In this instance, the retreatment window is a period of sixty minutes after the date and time for the first treatment. The process may also permit multiple additional treatments of the same retina of patient within the retreatment window.

Although several embodiments have been described in detail for purposes of illustration, various modifications may be made without departing from the scope and spirit of the invention. Accordingly, the invention is not to be limited, except as by the appended claims.

What is claimed is:

1. A process for controlling the number of uses of a retinal stimulation device on a patient, comprising the steps of:
   providing a retinal photostimulation device comprising a radiant energy source and projection optics configurable so as to target a retina of a person, a camera configurable so as to focus on and capture an image of the retina of the person simultaneously with the targeting of the retina by the radiant energy source and the projection optics, a monitor configurable so as to display the image of the retina captured by the camera, and electronic memory configured to record one or more images of the retina captured by the camera;
   beginning a treatment cycle for a patient using the retinal photostimulation device;
   registering the patient for a first treatment during the treatment cycle, including recording in a patient file in the electronic memory the patient's name, a date and time for the first treatment, and an identifying image of a retina of the patient;
   applying radiant beams from the radiant energy source to at least a portion of the retina of the patient so as to effect the first treatment contemporaneously with the date and time for the first treatment;
   permitting one or more additional treatments of the retina during the treatment cycle when the image of the retina of the patient corresponding to the one or more additional treatments biometrically matches the image of the retina of the patient corresponding to the first treatment and when the one or more additional treatments are within a predetermined retreatment window after the first treatment;
   preventing additional treatment of the retina during the treatment cycle when the retina corresponding to the additional treatment biometrically matches the image of the retina of the patient corresponding to the first treatment and the additional treatment is outside of the predetermined retreatment window after the first treatment; and
   ending the treatment cycle for the patient.

2. The process of claim 1, including the step of recording in the patient file a post-treatment image of the retina of the patient corresponding to the first treatment.

3. The process of claim 1, further comprising the step of registering the patient for a second treatment during the treatment cycle, including recording in the patient database the patient's name, a date and time for the second treatment, and an image of a second retina of the patient corresponding to the second treatment.

4. The process of claim 3, further comprising the step of preventing application of the second treatment during the treatment cycle when the image of the second retina of the patient corresponding to the second treatment biometrically matches the image of the retina of the patient corresponding to the first treatment.

5. The process of claim 4, wherein the preventing step further comprises preventing application of the second treatment during the treatment cycle, unless the date and time for the second treatment is within a predetermined retreatment window after the first treatment.

6. The process of claim 5, wherein the retreatment window comprises a period of sixty minutes after the date and time for the first treatment.

7. The process of claim 3, further comprising the step of permitting application of the second treatment during the treatment cycle when the image of the second retina of the patient corresponding to the second treatment does not biometrically match the image of the retina of the patient corresponding to the first treatment.

8. The process of claim 7, further comprising the step of recording in the patient file a post-treatment image of the second retina of the patient corresponding to the second treatment.

9. The process of claim 1, wherein the retreatment window comprises a period of sixty minutes after the date and time for the first treatment.

* * * * *